United States Patent [19]

Bertrand et al.

[11] Patent Number: 5,426,215
[45] Date of Patent: Jun. 20, 1995

[54] PROCESS FOR CONVERTING [R(−)-2(3-BENZOYLPHENYL)-PROPIONIC ACID TO THE S(+) ISOMER]

[75] Inventors: Claude Bertrand, Saint Germain Les Corbeil; Elie Fouque, Saint Maur Des Fosses; Isidore Le Fur, Thiais; Jean-Paul Richard, Corbeil, all of France

[73] Assignee: Rhone-Poulenc Rorer, S.A., Cedex, France

[21] Appl. No.: 213,477

[22] Filed: Mar. 16, 1994

Related U.S. Application Data

[63] Continuation of Ser. No. 976,977, filed as PCT/FR91/00670, Aug. 19, 1991, published as WO/03404, Mar. 5, 1992, abandoned.

[30] Foreign Application Priority Data

Aug. 20, 1990 [FR] France .................................. 9010460

[51] Int. Cl.$^6$ .............................................. C07B 57/00
[52] U.S. Cl. ..................................... 562/401; 562/402; 562/460; 562/494
[58] Field of Search ................. 562/401, 402, 460, 494

[56] References Cited

U.S. PATENT DOCUMENTS

| | | | |
|---|---|---|---|
| 4,209,638 | 6/1980 | Nicholson et al. | 562/402 |
| 4,983,765 | 1/1991 | Lukas et al. | 562/401 |
| 5,162,576 | 11/1992 | Manimaran et al. | 562/401 |

*Primary Examiner*—José G. Dees
*Assistant Examiner*—Dwayne C. Jones
*Attorney, Agent, or Firm*—Morgan & Finnegan

[57] ABSTRACT

Process for transforming (benzoyl-3-phenyl)-2-propionic-R(−) acid into an S(+) isomer through the action of a base either in situ during the splitting of racemic ketoprofen or on the crystallization mother liquor of a (benzoyl-3-phenyl)-2-propionic-S(+) acid salt.

25 Claims, No Drawings

PROCESS FOR CONVERTING [R(−)-2(3-BENZOYLPHENYL)-PROPIONIC ACID TO THE S(+) ISOMER]

This is a continuation of application Ser. No. 07/976,977, filed as PCT/FR91/00670, Aug. 19, 1991, published as WO/03404, Mar. 5, 1992, now abandoned.

FIELD OF THE INVENTION

The present invention relates to a process for converting [R(−)]-2-(3-benzoylphenyl)propionic acid to the S(+) isomer.

BACKGROUND OF THE INVENTION 2-(3-Benzoylphenyl)propionic acid (or ketoprofen) exhibits particularly useful anti-inflammatory, analgesic and/or antipyretic properties.

Ketoprofen, in the racemic form, consists of an equimolar mixture of S(+) and R(−) enantiomers.

Whereas in animals no substantial differences exist between racemic ketoprofen and the S(+) isomer, [S(+)]-ketoprofen, it has been shown in humans that [S(+)]-ketoprofen constitutes the active form of ketoprofen and that the R(−) isomer is not converted to the S(+) isomer.

It is particularly advantageous to be able to obtain [S(+)]-ketoprofen practically free from the R(−) isomer.

[S(+)]-Ketoprofen may be obtained by resolution of the racemic ketoprofen either by physicochemical methods (high-performance liquid chromatography with a chiral phase) or by formation of a salt with an optically active base.

These processes result in the production of the S(+) isomer and the R(−) isomer, the latter not having an inherent usefulness. It is therefore particularly important to be able to have available a process which makes it possible to convert [R(−)]-ketoprofen to [S(+)]-ketoprofen.

DESCRIPTION OF THE INVENTION

It has now been found, and that is what constitutes the subject of the present invention, that [R(−)]-ketoprofen may be converted either in situ during resolution of the racemic ketoprofen using in particular the resolving agent as converting agent, or from the resolution filtrates after having optionally removed the chiral base by treating with a strong base. Sodium hydroxide may be used as strong base.

According to the invention, the process is implemented in situ using, as resolving agent, a chiral base like cinchonidine and, as solvent, a ketone such as methyl isobutyl ketone or an alcohol such as ethanol. It is advantageous to use methyl isobutyl ketone which makes it possible to carry out the procedure at high temperatures. To obtain an improved yield, it is particularly advantageous to induce crystallization of the preponderant desired salt (cinchonidine salt of [S(+)]-ketoprofen) by concentrating the solution under reduced pressure.

Generally, one mole of cinchonidine is used per mole of ketoprofen.

Generally, the concentration procedure under reduced pressure is controlled in such a manner that the boiling temperature is constant and close to 100° C. during the entire duration of concentration. The crystals of the [S(+)]-ketoprofen salt which are formed are separated by filtration at a high temperature.

The conversion may also be achieved independently of crystallization, from crystallization mother liquors after eliminating the chiral base used as resolving agent and using an achiral base such as sodium hydroxide.

In order to implement the process using crystallization mother liquors, the resolution of racemic ketoprofen is first carried out using 0.5 to 1 mole of cinchonidine per mole of ketoprofen. After separation of the cinchonidine salt of ketoprofen (mainly [S(+)]-ketoprofen) by filtration, the mother liquors are treated with an aqueous solution of a strong inorganic base such as sodium hydroxide after release and separation of cinchonidine either in the base form or in the salt form. Ketoprofen (mainly [R(−)]-ketoprofen), in the form of the sodium salt, remains in the basic aqueous solution which is heated at a temperature generally above 100° C., preferably close to 110° C. while monitoring the variation of the optical titre as a function of time, the optical titre being expressed by the relationship $100 \times R/(R+S)$. The conversion is characterized by a progressive decrease of the optical titre.

EXAMPLES

The following examples show how the invention may be implemented in practice.

EXAMPLE 1

Resolution—Racemization 26.5 g of racemic ketoprofen (0.104 mole), 31 g of cinchonidine (0.105 mole) and 120.6 g (or 151 cm³) of methyl isobutyl ketone (1,204 mole) are introduced into a 250 cm³ reactor. The mixture is heated, with stirring, at 100° C. and then the mixture is concentrated under reduced pressure by setting the pressure such that the boiling temperature remains constant and equal to 100° C. 97.2 g of methyl isobutyl ketone are distilled in 8 hours. The mixture is stirred overnight at 100° C., for 45 minutes at 45° C. and then the reaction mixture is poured on a thermostated filter at 100° C. The filtration cake is washed with 70 cm³ of methyl isobutyl ketone at 20° C. and then dried. 19 g of ketoprofen salt are thus obtained whose optical titre (S/R+S) is 88.3%.

The yield is 58.6%.

Evaluation of ketoprofen gives the following results:

|  | Ketoprofen (g) | Optical titer (R/S) | Ketoprofen S(+) (g) | Ketoprofen R(−) (g) |
| --- | --- | --- | --- | --- |
| Isolated product | 8.80 | 11.7/88.3 | 7.77 | 1.03 |
| Mother liquors | 8.40 | 54.7/45.3 | 3.8 | 4.6 |
| Washings | 9.30 | 50.2/49.8 | 4.6 | 4.7 |

EXAMPLE 2

Racemization Using Sodium Hydroxide 10.4 g of racemic ketoprofen (0.041 mole), 6 g of cinchonidine (0.020 mole ) and 28.9 g ( or 36 cm³) of methyl isobutyl ketone (0.288 mole) are introduced into a reactor. The mixture is heated at 75° C., is then maintained at this temperature until complete dissolution and is then rapidly cooled to 70° C. Crystallization is started using a few crystals of cinchonidine salt of [S(+)]-ketoprofen. The slurry obtained is cooled over 6 hours from 70° C. to 10° C. at a rate of about −10° C. per hour. The slurry is filtered at a temperature close to 20° C. The filtration cake is washed with 15 g of methyl isobutyl ketone. 7.3 g of a salt are thus obtained whose composition is as follows:

—cinchonidine salt of [S(+)]-ketoprofen: 5.9 g (0.011 mole)
—cinchonidine salt of [R(−)]-ketoprofen: 1.4 g (0.002 mole).

The yield is 53.6%.

The filtrates have the following composition:
—[S(+)]-ketoprofen: 2.5 g (0.010 mole)
—[R(−)]-ketoprofen: 4.5 g (0.018 mole)
—cinchonidine: 2.1 g (0.007 mole).

22.1 g of 10% (w/w) aqueous sodium hydroxide, or 0.055 mole, are added, at room temperature, to a reaction mixture whose mass is 53 g.

Cinchonidine remains in the organic phase whereas ketoprofen, in the form of the sodium salt, remains in the aqueous phase. The aqueous phase is extracted with 32 g (or 40 cm$^3$) of methyl isobutyl ketone and then refluxed for 24 hours at 110°–115° C. Variation of the optical titre as a function of time is determined. The results are presented in the following table:

| Time (hours) | Optical; titer expressed as ketoprofen 100 × R/(R + S) |
| --- | --- |
| 0.0 | 64.8 |
| 2.3 | 59.6 |
| 4.6 | 56.8 |
| 21.5 | 50.9 |

EXAMPLE 3

Racemisation Using Sodium Hydroxide

There is introduced into a 300 liter enamelled reactor 175 liters (145.3 kg) of a filtrate from the resolution of racemic ketoprofen using cinchonidine in ethanol whose composition is as follows:

—cinchonidine salt of ketoprofen: 23.07 kg (42.04 moles) [optical purity of ketoprofen (S/S+R) close to 30%]
—ethanol: 155 liters (122.23 kg)

The ethanolic solution is concentrated under reduced pressure (80 mm of mercury; 10.7 kPa) at 30° C. until a thick mass is obtained to which 57.7 liters (50 kg) of toluene are added and then 20 liters of solvent are again distilled.

42 liters of distilled water and 18.5 liters of 9.8 N hydrochloric acid are added to the toluene-containing solution heated at 50° C. by a water-vapor mixture in a double jacket. The mixture is vigorously stirred until the temperature of the reaction mixture again reaches 50° C. After stopping the stirring and decanting, the bottom aqueous phase is separated and the organic phase is washed with 1 N hydrochloric acid.

35 liters of distilled water and 3.1 liters of 9.8 N hydrochloric acid are added to the organic phase maintained at 50° C. The mixture is vigorously stirred for 10 minutes. After decanting, the aqueous phase is combined with the previously separated aqueous phases.

The organic phase is washed with 35 liters of distilled water containing 1.5 liters of 9.8 N hydrochloric acid and then with 30 liters of distilled water. The washings are removed.

The previous toluene-containing solution is added to a solution of 16.5 liters of 10 N sodium hydroxide (21.9 kg, 165 moles) in 16 liters of distilled water. The mixture is vigorously stirred and then heated to 100° C. (live vapor in the double jacket). The reaction mixture is maintained under reflux for 12 hours.

After cooling and after decanting, the reaction mixture consists of 3 phases:

1) a milky bottom phase (11.9 kg) which is separated and removed,
2) a slightly yellow middle phase (39 kg) which contains the sodium salt of ketoprofen,
3) a colorless toluene-containing top phase.

Analysis of the middle phase by chiral HPLC shows that the optical titre (S/S+R) is 50%: the racemisation is complete.

20 liters of toluene and 13 liters of 9.8 N hydrochloric acid are added to the middle phase heated to 50° C. The mixture is vigorously stirred. After decanting, the aqueous phase is exhaustively extracted with 20 liters of toluene.

The toluene-containing phases are combined and then concentrated by distillation of 29 liters of toluene under reduced pressure (80 mm of mercury; 10.7 kPa) at 42° C.

Cyclohexane is added to the concentrated toluene-containing solution heated to 70° C. such that the cyclohexane-toluene ratio is 6–4 (w/w) that is 23 liters of cyclohexane.

The mixture is cooled to 60° C. and then the recrystallization is started by adding 50 g of racemic ketoprofen.

After cooling to a temperature close to 15° C., the slurry is filtered and then washed 2 times with a mixture of 3.5 liters of toluene and 6 liters of cyclohexane.

A filtration cake is thus obtained which represents 9.76 kg of dry ketoprofen and which is used as it is in a new resolution procedure.

The ketoprofen assay, determined by non-chiral HPLC, is 100%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for converting {R(−)}-2-(3-benzoylphenyl) propionic acid to the S(+) isomer, comprising combining {R(−)}-ketoprofen with a base and a ketone as a solvent and heating at a temperature from 100° C. to 115° C. to convert {R(−)}-ketoprofen to the S(+) isomer.

2. Process according to claim 1, wherein the conversion of {R(−)}-ketoprofen to {S(+)}-ketoprofen is carried out in situ during the resolution of racemic ketoprofen.

3. Process according to claim 1, wherein the conversion of {R(−)}-ketoprofen to {S(+)}-ketoprofen is carried out using the crystallization mother liquors of an {S(+)}-ketoprofen salt.

4. Process according to claim 2, wherein chiral base is used as converting agent and as resolving agent.

5. Process according to claim 4, wherein the chiral base is cinchonidine.

6. Process according to claim 2, wherein one mole of converting agent is used per mole of racemic ketoprofen.

7. Process according to claim 2, wherein said ketone is methyl isobutyl ketone.

8. Process according to claim 2, wherein it is carried out at a temperature about 100° C.

9. Process according to claim 3, wherein a strong base is used after the optional elimination of the resolving agent.

10. Process according to claim 3, wherein the strong base is sodium hydroxide.

11. Process according to claim 3, wherein the mother liquors are obtained from resolution of the racemic ketoprofen by means of a chiral base by working in an organic solvent.

12. Process according to claim 11, wherein the chiral base is cinchonidine.

13. Process according to claim 11, wherein 0.5 mole of chiral base is used per mole of ketoprofen.

14. Process according to claim 11, wherein the ketone is methyl isobutyl ketone.

15. Process according to claim 3, wherein a molar excess of base is used relative to the ketoprofen present in the mother liquors.

16. Process according to claim 3, wherein it is carried out at a temperature above 100° C.

17. Process according to claim 16, wherein the temperature is between 110° and 115° C.

18. Process for in situ conversion of $\{R(-)\}$-2-(3-benzoylphenyl) propionic acid to the S(+) isomer comprising the steps of:
   (a) combining said $\{R(-)\}$-2-(3-benzoylphenyl) propionic acid, a chiral base as a resolving agent and a ketone as a solvent in a reactor;
   (b) heating the combined components of step (a) to dissolve said $\{R(-)\}$-2-(3-benzoylphenyl) propionic acid and said chiral base in said solvent to form a solution;
   (c) concentrating said solution by reducing pressure in said reactor to maintain said solution at a constant boiling temperature of about 100° C. and thereby induce crystallization; and
   (d) filtering the concentrated solution of step (c) to remove crystals of a $\{S(+)\}$-ketoprofen salt.

19. Process of claim 18 further comprising the steps of cooling said solution of step (b); and seeding said solution with crystals of a salt of $\{S(+)\}$-ketoprofen to initiate crystallization.

20. Process according to claim 18 further comprising the steps of:
   (e) retaining the filtered solution of step (d) as a mother liquor;
   (f) treating said mother liquor with a strong inorganic base to remove said chiral base with mainly $\{R(-)\}$-ketoprofen in the form of sodium salt remaining in the thus formed basic aqueous solution; and
   (g) heating the basic aqueous solution formed in step (f) at a temperature from 100° C. to 115° C. while monitoring variation of the optical titre of the basic aqueous solution as a function of time, whereby conversion to the S(+) isomer is shown by a progressive decrease of the monitored optical titre.

21. Process according to claim 18 wherein said chiral base is cinchonidine.

22. Process according claim 21 wherein the molar ratio of cinchonidine to ketoprofen in step (a) is 1:1.

23. Process according to claim 24 wherein the solution of step (a) includes 0.5 to 1.0 mole of cinchonidine per mole of ketoprofen.

24. Process according to claims 21 wherein said solvent is methyl isobutyl ketone.

25. Process according to claim 18 wherein said solvent is methyl isobutyl ketone.

* * * * *